US00RE39351E

(19) United States
(12) Reissued Patent
Vinik et al.

(10) Patent Number: US RE39,351 E
(45) Date of Reissued Patent: Oct. 17, 2006

(54) HIGH LEVEL OF EXPRESSION OF INGAP IN BACTERIAL AND EUKARYOTIC CELLS

(75) Inventors: Aaron I. Vinik, Norfolk, VA (US); Gary L. Pittenger, Virginia Beach, VA (US); Ronit Rafaeloff-Phail, Indianapolis, IN (US); Scott W. Barlow, Norfolk, VA (US)

(73) Assignee: Eastern Virginia Medical School of the Medical College of Hampton, Norfolk, VA (US)

(21) Appl. No.: 09/659,379

(22) Filed: Sep. 8, 2000

Related U.S. Patent Documents

Reissue of:
(64) Patent No.: 5,804,421
Issued: Sep. 8, 1998
Appl. No.: 08/909,725
Filed: Aug. 12, 1997

U.S. Applications:
(63) Continuation-in-part of application No. 08/741,096, filed on Oct. 30, 1996, now abandoned.

(51) Int. Cl.
*C12P 21/06* (2006.01)

(52) U.S. Cl. ..... 435/69.1; 435/6; 435/7.1; 435/320.1; 435/325; 435/252.3; 536/23.1; 536/23.5; 536/24.1; 530/350

(58) Field of Classification Search ..... 435/69.1, 435/252.3, 320.1, 6, 325, 7.1; 536/23.1, 23.5, 536/24.1; 530/350
See application file for complete search history.

(56) References Cited

U.S. PATENT DOCUMENTS

| | | | | | |
|---|---|---|---|---|---|
| 4,439,521 | A | * | 3/1984 | Archer et al. | 435/1 |
| 4,935,000 | A | * | 6/1990 | Dudek | 600/36 |
| 4,965,188 | A | * | 10/1990 | Mullis et al. | 435/6 |

FOREIGN PATENT DOCUMENTS

| | | |
|---|---|---|
| EP | 0 383 453 A1 | 8/1990 |
| WO | WO 91/16428 | 10/1991 |
| WO | WO 96/26215 | 8/1996 |

OTHER PUBLICATIONS

Ronit Rafaeloff et al, Cloning and Sequencing of the Pancreatic Islet Neogenesis Associated Protein (INGAP) Gene and its Expression in Islet Neogenesis in Hamsters, J. Clin. Invest, 1997, vol. 99, No. 9, pp. 2100–2109.

Patent Abstracts of Japan, Publication No. 06135998, Publication Date of May 17, 1994.

Stein et al., "Antisense Oligonucleotides as Therapeutic Agents—Is the Bullet Really Magical?", *Science* 261:1004–1012 (1993).*

Bradley et al., "BioTechnology. Modifying the Mouse", *Design and Desire* 10:534–539 (1992).*

Miller et al., "Human Gene Therapy Comes of Age", *Nature* 357:455–460 (1992).*

Watanabe et al., "Pancreatic Beta–Cell Replication and Amelioration of Surgical Diabetes by Reg Protein", *Proc. Natl. Acad. Sci. USA* 91:3589–3592 (1994).*

Liang et al., "Distribution and Cloning of Eukaryotic mRNAs by Means of Differential Display: Refinements and Optimization", *Nucleic Acids Research* 21(14):3269–3275 (1993).*

Lu et al. (Apr. 11, 1996) Nature, vol. 380, pp. 544–547.*

Rosenberg et al., "Reversal of Diabetes by the Induction of Islet Cell Neogenesis", *Transplantation Proceedings* 24(3):1027–1028 (1992).*

Rouquier et al., "Rat Pancreatic Stone Protein Messenger RNA",*J. Biol. Chem.,* 266(2):786–791 (1991).*

Lasserre et al., "A Novel Gene (HIP) Activated in Human Primary Liver Cancer",*Cancer Research* 52:5089–5095.*

Terazono et al., "A Novel Gene Activated in Regenerating Islets", *J. Biol. Chem.,* 263(5):211–2114 (1988).*

Vinik et al., "Factors Controlling Pancreatic Islet Neogenesis", *Yale Journal of Biology and Medicine* 65:471–491 (1992).*

Orelle et al., "Human Pancreatitis–associated Protein" *J. Clin. Invest.* 90:2284–2291 (1992).*

Pittenger et al., "The Partial Isolation and Characterization of Ilotropin, a Novel Islet–Specific Growth Factor", *Adv. Exp. Med. Biol.* 321:123–130 (1992) Abstract.*

Rosenberg, et al., "Trophic Stimulatin of th eDuctular–Islet Cell Axis: A New Approach to the Treatment of Diabetes", *Pancreatic Islet Cell Rgeneration and Growth,* edited by A. I. Vinik, Plenum Press, New York, 1992.*

* cited by examiner

*Primary Examiner*—Jon Weber
*Assistant Examiner*—Hope A. Robinson
(74) *Attorney, Agent, or Firm*—Banner & Witcoff, Ltd.

(57) ABSTRACT

Removal of the nucleotide sequence encoding the signal peptide from the INGAP coding sequence allows cultured cells to express substantial amounts of INGAP activity. Previous attempts have provided only low yields of INGAP, possibly because the signal sequence of INGAP is toxic to the cells.

49 Claims, 2 Drawing Sheets

HIGH LEVEL OF EXPRESSION OF INGAP IN BACTERIAL AND EUKARYOTIC CELLS

Matter enclosed in heavy brackets [ ] appears in the original patent but forms no part of this reissue specification; matter printed in italics indicates the additions made by reissue.

This is a continuation-in-part application of U.S. Ser. No. 08/741,096, filed Oct. 30, 1996, now abandoned *which is a re-issue application of Ser. No. 08/909,725 filed Aug. 12, 1997, U.S. Pat. No. 5,804,421.*

TECHNICAL FIELD OF THE INVENTION

This invention is related to methods and constructs for achieving high level expression of INGAP, a protein involved in islet cell neogenesis.

BACKGROUND OF THE INVENTION

Pancreatic islets of Langerhans are the only organs of insulin production by β cells in the body. However, they have a limited capacity for regeneration. This limited regeneration capacity predisposes mammals to develop diabetes mellitus. Thus there is a need in the art of endocrinology for products which can stimulate the regeneration of islets of Langerhans to prevent or ameliorate the symptoms of diabetes mellitus.

There are many factors regulating pancreatic β cell mass. (Vinik, et al., Diabetes Reviews 4: 235–263, 1996.) A pancreatic extract called ilotropin induces β cell regeneration and reverses diabetes. (Rosenberg et al. (1996) Diabetologia 39: 256–262. A gene encoding a protein within ilotropin has been identified and isolated; the protein is responsible for stimulating islet cell regeneration. (Rafaeloff, R. Journal of Clinical Investigations 99: 2100–2109, 1997.) This protein is called INGAP, and is disclosed in patent applications Ser. Nos. 08/401,530, 08/709,662, and 60/006,271. The disclosure of these applications is expressly incorporated herein. Despite the knowledge of the complete nucleotide sequence of the INGAP gene, expression of the protein has been limited. Thus there is a need in the art for methods of expressing and isolating large quantities of the INGAP protein, especially in eukaryotic systems.

SUMMARY OF THE INVENTION

It is an object of the present invention to provide a method of producing biologically active INGAP [protein] from a recombinant host cell.

It is another object of the present invention to provide a host cell which expresses large amounts of INGAP [protein].

It is an object of the present invention to provide a recombinant construct for expression of biologically active INGAP [protein].

Another object of the invention is to provide a method for isolating INGAP [protein] from a recombinant host cell.

These and other objects of the invention are achieved by providing the art with a recombinant construct for expression of biologically active INGAP [protein] comprising:

a first nucleotide sequence encoding amino acids 27 to 175 SEQ ID NO: 6 operably linked to a transcriptional initiation site and a translational initiation site, wherein a second nucleotide sequence encoding a signal peptide is not present immediately 5' of said first nucleotide sequence.

In another embodiment of the invention a method of producing INGAP activity from a recombinant host cell is provided. The method comprises the steps of:

culturing a host cell comprising a recombinant construct comprising a first nucleotide sequence encoding amino acids 27 to 175 SEQ ID NO: 6 operably linked to a transcriptional initiation site and a translational initiation site, wherein a second nucleotide sequence encoding a signal peptide is not present immediately 5' of said first nucleotide sequence;

recovering protein from said cultured host cell.

In yet another embodiment of the invention a host cell is provided. The host cell comprises a recombinant construct comprising a first nucleotide sequence encoding amino acid[s] *residues* 27 to 175 *of* SEQ ID NO: 6 operably linked to a transcriptional initiation site and a translational initiation site, wherein a second nucleotide sequence encoding a signal peptide is not present immediately 5' of said first nucleotide sequence. These and other embodiments of the invention which will be apparent to those of skill in the art provide a practical source of INGAP [protein] in amounts suitable for use in preclinical and clinical situations.

DETAILED DESCRIPTION

Figure 1:
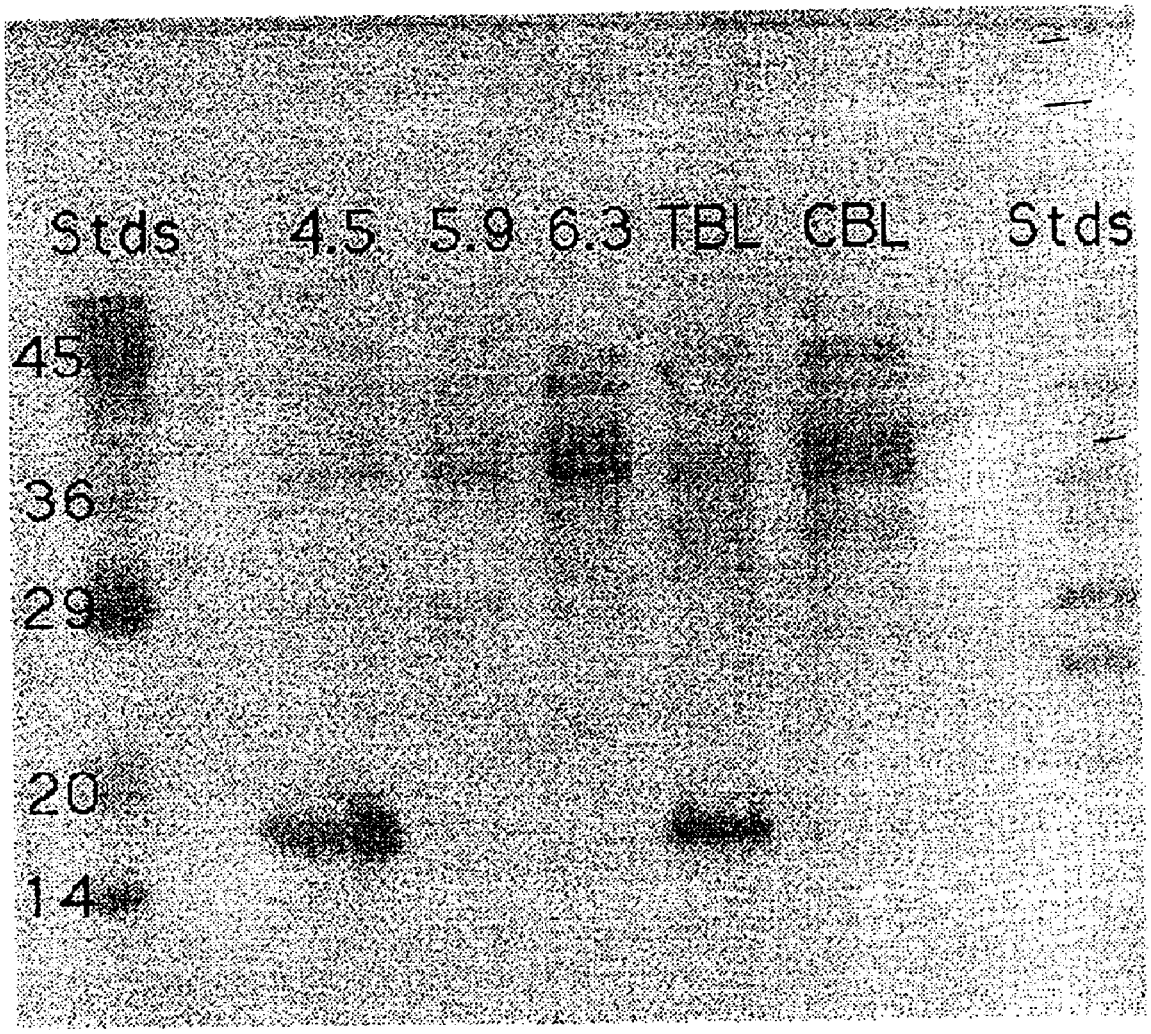
FIG. 1. SDS-PAGE gel of products of bacterial transfection. Bacterial lysate without transfection (CBL), bacterial lysate with transfection (TBL), fractions from Ni-NTA chromatography (eluted at pH6.3 (6.3); pH 5.9 (5.9); and pH 4.5 (4.5) and standards (Std).

It is a discovery of the present inventors that bacterial expression as well as eukaryotic expression of INGAP can be achieved at high levels by deleting the coding sequence of the signal sequence of INGAP. While not wanting to be bound by any particular theory or mechanism of action, applicants believe that the signal sequence is toxic to host systems. The signal sequence comprises amino acids 1 to 26 as shown in SEQ ID NO: 5. In the constructions tested, the 5' untranslated region comprising nucleotides 1–16 SEQ ID NO. 1 has also been deleted. This deletion may also contribute to the increase in expression which has been observed.

Applicants have found that an inducible transcription initiator is exceedingly useful for INGAP expression in prokaryotic systems. Suitable inducible transcription initiators include the lac promoter/operator, the tac promoter, the trp promoter, the λcI promoter, the tet promoter, as well as others which are known in the art.

According to another aspect of the invention, a histidine tag can be put on the protein. The histidine tag can simplify processing and purification. A histidine tag is a stretch of histidine residues which is appended to a protein, usually by genetic engineering. Preferably the tag comprises between 3 and 12 histidine residues. They may be contiguous or interrupted by other residues. The histidine tag may be appended to the N-terminal or to the C-terminal end of the protein to minimize disruption of protein function. Methods for making and utilizing histidine tags are known in the art. The oligohistidine can be used as an affinity moiety using a metal chelate, such as nickel-NTA (N-(5-amino-1-carboxypentyl)-iminodiacetic acid) as the other affinity partner.

A recombinant construct according to the invention, is any DNA molecule which has been engineered so that two segments of DNA are adjacent to each other which are not adjacent to each other in nature. Preferably, such engineering is performed in vitro, although in vivo engineering can also be performed. The construct may be a plasmid, phage, virus, transposable element, minichromosome, or other elements, as is suitable for the desired application.

In a preferred embodiment, the construct for INGAP expression in eukaryotic systems contains an origin of replication, e.g., ERV oriP, which permits extrachromosomal maintenance in primate and canine cell lines. A sequence element which encodes a nuclear antigen and allows high level episomal replication, e.g., EBNA-1 or SV40 T antigen is also desirable.

The coding sequence of amino acid residues 27–175 of INGAP [protein] are included in the constructs. Preferably the entire signal sequence is deleted. However, it is possible that only a portion of the signal sequence must be deleted to obtain excellent expression. Thus some portion of the signal sequence might be retained in the constructs.

Deletion of the 5' untranslated region, nucleotides 1–16, is also desirable. However, it is not known if this is necessary to achieve excellent expression. Thus the 5' untranslated region may be retained in some constructs without departing from the spirit of the invention.

A host cell according to the invention can be transfected or transformed with a recombinant construct according to the present invention. The host may be a bacteria, yeast, insect, or mammalian cell. For eukaryotic expression of INGAP, any cell lines suitable for protein expression may be used, including COS-7 cells and CHO cells.

Selection of suitable promoters and translational initiators for use in the appropriate host cell is well within the ability of those skilled in the art. For eukaryotic expression system, it is exceedingly useful to choose a promoter sequence which is capable of initiating constitutive transcription to achieve constitutive high level expression of the protein. Rous sarcoma virus long terminal repeat (RSVLTR) is an example of such promoter, although others as are known in the art can be used.

Host cells may be transformed, transfected, mated or infected with the recombinant host cell of the present invention. Culturing of host cells can be performed using techniques and media which are well known in the art. Again, a suitable medium and technique can be selected by an ordinary skilled artisan.

The above disclosure generally describes the present invention. A more complete understanding can be obtained by reference to the following specific examples which are provided herein for purposes of illustration only, and are not intended to limit the scope of the invention.

EXAMPLE 1

This example describes the experimental design employed.

We generated a new INGAP cDNA by PCR which excluded the 5' UTR region (nucleotides 1–16 in SEQ ID: 1) and nucleotides encoding the signal peptide (nucleotides 17–94 SEQ ID NO: 1) and created two new restriction enzyme recognition sites enabling the insertion of the new construct into a new pQE-31 expression vector. This new ligated construct was transformed into TOP10F' competent cells (E. coli host strain from Invitrogen). The positive clones were identified, verified by restriction enzyme digestion and the DNA isolated. The DNA was now transformed into a different competent E. coli strain, M15(pREP4) and expression of the protein was induced by IPTG (isopropyl-beta, D-thiogalactopyranoside) which inhibits the repressor, facilitating expression of the protein from the M15 promoter/operator. The reason for the intermediate transformation of the ligated material into TOP10F' is that these cells are highly competent increasing the odds of getting insert positive colonies. The M15(pREP4) cells that were used for protein expression do not attain competency levels high enough to guarantee transformation of the ligation products. The resultant plasmid DNA obtained from the transformation of the TOP10F' was sufficient to enhance the transformation of the M15(pREP4) cells. The His-tagged protein was isolated by $Ni^{+2}$ agarose affinity purification.

We used a PCR approach to generate a new INGAP cDNA which excludes the 5' UTR region (nucleotides 1–16 in SEQ ID NO: 1) and nucleotides encoding the signal peptide.

The nucleotide sequence (SEQ ID NO: 1) and corresponding amino acid sequence (SEQ ID NO: 5) that have been excluded are as follows: (the bolded area represents the sequence of the signal peptide)

```
CTGCAAGACAGGTAACC   ATG ATG CTT CCC ATG ACC CTC TGT AGG
                    MET MET Leu Pro MET The Leu Cys Arg
ATG TCT TGG ATG CTG CTT TCC TGC CTG ATG TTC CTT TCT TGG
MET Ser Trp MET Leu Leu Ser Cys Leu MET Phe Leu Ser Trp
GTG GAA GGT
Val Glu Gly
```

EXAMPLE 2

This example describes the use of polymerase chain reaction to synthesize INGMAT (a construct which lacks the signal peptide sequence, i.e., which encodes the mature protein).

Oligonucleotide design:

Oligonucleotides for PCR were designed to incorporate restriction enzyme recognition sites at their respective 5' ends. The oligonucleotide designed for the 5' end of the gene incorporates a Bam HI site followed by 20 nucleotides corresponding to the N-terminus of the mature protein. The oligonucleotide designed for the 3' end incorporates an Xho I site followed by 20 untranslated nucleotides. The PCR product generated from these primers contains the mature INGAP sequence and the native protein termination codon.

The following is the sequence of the oligonucleotides used:

5' of INGAP (SEQ ID NO: 2)

5'-CCGCGGATCCCGAAGAATCTCAAAAGAAACT-3'

3' of INGAP (SEQ ID NO: 3)

5'-GACCGGCTCGAGTGCTCTTCCTGAGTGAATCC-3'

PCR of INGMAT

Reaction conditions

| | |
|---|---|
| Template: (50 ng INGAP original cDNA removed from pCDNA3) | 5 μl |
| $MgCl_2$: | 4 μl |
| 10 × PCR buffer | 5 μl |
| dATP | 1 μl |
| dCTP | 1 μl |
| dGTP | 1 μl |
| dTTP | 1 μl |
| 5' primer | 1 μl |
| 3' primer | 1 μl |
| $H_2O$ | 29 μl |
| Taq polymerase | 1 μl |
| total volume = | 50 μl |

cycle parameters

A) 2 min at 95° C.

B) 30 cycles of (1 min 95° C., 1 min 55° C., 1 min 72° C.)

C) 7 min at 72° C.

D) 4° C. until removed from thermal cycler.

The PCR products were then electrophoresed on a 5% PAGE in TBE. Ethidium bromide stained PCR products corresponding to the expected size for the construct were cut from the gel. The gel fragments were electro-eluted into 0.5 ml of TBE, precipitated with 50 μl 3M sodium acetate and 1 ml of isopropanol at −80° C. for 20 min, centrifuged, washed once with 1 ml of isopropanol, washed once with 1 ml of 70% ethanol, and then dried under vacuum. The dried pellet was resuspended in 50 μl $H_2O$ and quantified. At the end of this step the sequence of the PCR product that contains both restriction sites minus the signal sequence and 5' UTR was as follows (SEQ ID NO: 4):

5'-CC GCG GAT CCC GAA GAA TCT CAA AAG AAA CTGCCT

TCT TCA CGT ATA ACC TGT CCT CAA GGC TCT GTA GCC TAT

GGG TCC TAT TGC TAT TCA CTG ATT TTG ATA CCA CAG ACC

TGG TCT AAT GCA GAA CTA TCC TGC CAG ATG CAT TTC TCA

GGA CAC CTG GCA TTT CTT CTC AGT ACT GGT GAA ATT ACC

TTC GTG TCC TCC CTT GTG AAG AAC AGT TTG ACG GCC TAC

CAG TAC ATC TGG ATT GGA CTC CAT GAT CCC TCA CAT GGT

ACA CTA CCC AAC GGA AGT GGA TGG AGG TGG AGC AGT

TCC AAT GTG CTG ACC TTC TAT AAC TGG GAG AGG AAC CCC

TCT ATT GCT GCT GAC CGT GGT TAT TGT GCA GTT TTG TCT

CAG AAA TCA GGT TTT CAG AAG TGG AGA GAT TTT AAT TGT

GAA AAT GAG CTT CCC TAT ATC TGC AAA TTC AAG GTC TAG

GGC AGT TCT AAT TTC AAC AGC TTG AAA ATA TTA TGA AGC

TCA CAT GGA CAA GGA AGC AAG TAT GAG GAT TCA CTC

AGG AAG AGC ACT CGA GCC GGT C-3'

*The bolded areas represent the primers.

EXAMPLE 3

This example describes the creation of a plasmid containing the expression construct.

Restriction enzyme digestion of the INGMAT PCR product and the pQE-31 vector

We performed two parallel restriction enzyme digestion reactions using 2.5 μg of both the INGMAT PCR product and pQE-31 vector. INGMAT was digested with Bam HI and Xho I simultaneously in a 30 μl volume. PQE-31 was digested with Bam HI and Sal I simultaneously in a 30 μl volume. Both digestion reactions were carried out at 37° C. for a period of 4 hours. After the reactions were completed, 400 ng of each was electrophoresed on a 1.5% agarose gel and stained with ethidium bromide to assure complete digestion. The remainder (~2.1 ug) of both digestion reactions were passed over a sepharose G-50 to remove the small DNA fragments followed by two equal volume phenol extractions. The extracted DNA was then precipitated with 2 volumes of ethanol and 1/10 volume 3M sodium acetate at −80° C. for 20 minutes, centrifuged, washed twice with 70% ethanol and dried under vacuum. The pellets were resuspended in 25 μl $H_2O$ and quantified.

The pQE-31 expression system was purchased from QIAGEN Inc. Chatsworth, Calif.

Ligation of INGMAT into pQE-31

INGMAT (Bam HI/Xho I) and pQE-31(Bam HI/Sal I) have compatible ends suitable for ligation. As a result of the ligation the Sal I restriction site in the vector will be eliminated.

Ligation conditions using a 2:1 vector to insert molar ratio.

| | |
|---|---|
| pQE31(vector) 517 ng | 9 μl |
| INGMAT (insert) 165 ng | 2.5 μl |
| 10 × ligation buffer | 5 μl |
| 10 mM rATP | 5 μl |
| T4 Ligase 4u | 1 μl |
| $H_2O$ | 27.5 μl |
| final volume = | 50 μl |

The ligation reactions were incubated at 4° C. for 16 hours.

Transformation of the ligation reaction products into TOP10F' competent E. coli

We removed 5 μl of the ligation reaction into 100 μl of competent TOP10F' cells, (TOP10F' cells were purchased from Invitrogen, San Diego, Calif.) with 0.5 μl of 500 mM β-mercaptoethanol and incubated on ice for 30 minutes, heat shocked for 45 seconds at 42° C., and recovered on ice for 2 minutes. Then we added 1 ml of prewarmed S° C. media and incubated at 37° C. with shaking at 225 rpm for 1 hour followed by plating all the transformation reaction on LB broth agar plates containing 100 μg/ml ampicillin.

Selection of transformants

Colony containing plates were lifted onto Nytran membranes. The colonies were lysed with 0.5M NaOH, neutralized, and the resultant DNA bound to the membrane by baking at 80° C. for 1 hour. The membranes were then hybridized in 50% formaldehyde, 5×SSPE at 50° C. for 16 hours with $3\times10^6$ cpm/ml of $^{32}P$ random primed INGAP cDNA. The membranes were washed at high stringency and exposed to X-ray film. Positive colonies were matched up to the X-ray film and grown up in 3 mls of LB with ampicillin.

DNA isolation from positive transformants

DNA was isolated from the small cultures using alkaline lysis, phenol extracted, precipitated, dried, and resuspended in 50 μl $H_2O$. A small aliquot of each of the isolated DNA were digested with Bam HI and Hind III to release inserts. The digested DNAs were electrophoresed on 1.5% agarose and stained with ethidium bromide and positive inserts identified at approximately 510 bp size range. We took four of the insert containing plasmids and incubated them in the presence of RNAse to remove any residual bacterial RNA.

Transformation of the ligation products into MIS (pREP4) competent E. coli

We removed 5 μl of the cleaned DNA isolated in section IIE and transfer it into 100 μl of M15(pREP4) competent cells. The mixture was incubated on ice for 30 minutes, heat shocked for 45 seconds at 42° C., and recovered on ice for 2 minutes. 1 ml of prewarmed SOC media was added and incubated at 37° C. with shaking at 225 rpm for 90 minutes. All of the transformation reaction was plated on LB broth agar plates containing 100 μg/ml ampicillin and 25 μg/ml kanamycin.

Selection of transformants for INGMATHIS (INGMAT plus a six-histidine tag) protein production Eight colonies were picked and grown up in LB with ampicillin. DNA was isolated from the small cultures using alkaline lysis extraction procedures, phenol extracted, precipitated, dried, and resuspended in 50 μl $H_2O$. A small aliquot of each of the isolated DNA were digested with Bam HI and Hind III to release inserts. The digested DNA was run on 1.5% agarose gel and visualized by staining with ethidium bromide. Several of the transformants which demonstrated the plasmid with inserts of the correct size as well as the presence of the pREP4 plasmid were stored in 50% glycerol at −80° C. to be used for protein production.

EXAMPLE 4

This example describes denaturing metal affinity protein chromatography isolation of the his tagged INGAP protein without signal peptide. (Procedure for a 250 ml pINGMATHIS transformed M15(pREP4) culture. pINGMATHIS is the INGMATHIS construct ligated into the pQE-31 vector.)

Bacteria growth and protein induction

We grew a 25 ml overnight in LB with 100 g/ml ampicillin and 25 μg/ml kanamycin antibiotic. We started a 250 ml LB plus 100 μg/ml ampicillin and 25 μg/ml kanamycin culture with 5 ml of the overnight. (1:50) Grown until ABS600=0.0.75 to 0.9 (actual OD=0.866). Added 5 ml of 100 mM IPTG (2 mM final) to induce production of the protein. Continue growing for 4 hours in the case of INGAP. Collected the bacteria and spin at 6000 rpm for 20 minutes, discarded the supernatant. The pellet was frozen until ready to use at −70° C.

$Ni^{+2}$ NTA agarose preparation

Prepare as much as will be needed. (Use 10 ml of the 50% $Ni^{+2}$ NTA for each 250 ml derived bacterial pellet). Place 16 ml of the 50% slurry into a disposable 50 ml centrifuge tube. Centrifuge for 2 minutes at 800×g and discard the supernatant. Add 42 ml of sterile water, resuspend the resin. Centrifuge for 2 minutes at 800×G and discard the supernatant. Add 42 ml of sterile water, resuspend the resin. Centrifuge for 2 minutes at 800×G and discard the supernatant. Add 42 ml of binding/lysis buffer A (6M Guanidine HCl, 0.1M sodium phosphate, 0.01M Tris, pH 8.0) and resuspend the resin. Centrifuge for 2 minutes at 800×G and discard the supernatant. Add 42 ml of binding/lysis buffer A (6M Guanidine HCL, 0.1M sodium phosphate, 0.01M Tris, pH 8.0) and resuspend the resin. Centrifuge for 2 minutes at 800×G and discard the supernatant. Add 42 ml of binding/lysis buffer A (6M Guanidine HCL, 0.1M sodium phosphate, 0.01M Tris, pH 8.0) and resuspend the resin. Centrifuge for 2 minutes at 800×G and discard the supernatant. Bring the total volume up to 10 ml with buffer A. The slurry is now ready for the application of the lysed bacteria.

Bacteria lysis and protein isolation

Thaw the bacterial pellet for 15 minutes at room temperature. Resuspend the pellet in 12.5 ml of lysis buffer A. (6M Guanidine HCL, 0.1M sodium phosphate, 0.01M Tris, pH 8.0). Transfer the resuspension to a 50 ml centrifuge tube. Freeze the resuspension/lysate at −70 until solid. Thaw at room temperature. Place the lysate on a rotator for 60 minutes at room temperature. Centrifuge the lysate for 15 minutes at 10,000×G. Collect the supernatant and add the 10 ml of prepared Ni2+NTA. Rotate for 45 minutes. Load the slurry onto a 1.6 cm diameter column and allow to flow through by gravity.

Washes

Flow through 50 ml of buffer A. (No need to collect.) Flow through 40 ml of buffer B (8M Urea, 0.1M Sodium phosphate, 0.01M Tris, pH 8.0). (No need to collect.) but $A_{280}$ should be at or near zero before continuing, if not, then wash with more. Wash through 40 ml of buffer C, same as B but pH 6.3. Collect 3 ml fractions. Wash through 40 ml of buffer D, same as B but pH 5.9. Collect 3 ml fractions.

Wash through 40 ml of buffer E, same as B but pH 4.5. Collect 3 ml fractions. At this point the protein should be in one of the fractions taken. Read the absorbance at 280 of all the fractions to discern where the protein is. Pool, reduce, and SDS page electrophoresis as necessary.

Dialysis

In order to purify the expressed protein, we changed the carrier solution of the fraction extracted from the nickel/NTA at pH 4.5 to Tris buffer using dialysis. Dialysis tubing with a molecular weight cut-off of 3000 was prepared by boiling in 5 mM EDTA/200 mM sodium bicarbonate for 5 minutes. The tubing was rinsed briefly in deionized water and boiled another 5 minutes in the bicarbonate solution. The tubing was returned to deionized water, covered with aluminum foil and autoclaved for 10 minutes on a liquid cycle. The tubing was handled with latex gloves during the entire procedure.

One ml of the protein solution from the nickel/NTA column in 6M guanidine HCl was dialyzed against 4 liters of 25 mM Tris buffer at pH 8.5 for 12 hours. After dialysis, there were 2 mls of protein solution with a protein concentration of 800 ug/ml.

EXAMPLE 5

This example describes analytical techniques confirming the identity of the product.

SDS-PAGE

In order to test for the overexpression of [the] INGAP [protein], discontinuous denaturing polyacrylamide gel electrophoresis was performed on the dialyzed protein solution using the Hoefer SE250 Might Small II apparatus. The separating gel was prepared with 15% acrylamide, 1.35% bis-acrylamide in 375 mM Tris buffer at pH 8.8 with 0.05% sodium dodecyl sulfate. Polymerization was induced by addition of 0.05% ammonium persulfate and 20 μl TEMED/15 ml solution. The solution was placed in the gel plate apparatus for polymerization. The stacking gel was poured with the same solution, except the Tris buffer was 125 mM at pH 6.8, and the acrylamide concentration was 4%. The protein samples were diluted 1:1 with sample buffer (125 mM Tris-Cl, pH 6.8, 4% SDS, 20% glycerol, and 10% 2-mercaptoethanol).

The upper and lower tank buffers were identical, containing 25 mM Tris, 192 mM glycine and 0.1% SDS at pH 8.3. Two gels were loaded with 20 μl each of bacterial lysate without transfection (CBL,368 ug/ml), bacterial lysate with transfection (TBL, 341 ug/ml), the fractions from Ni-NTA chromatography (eluted at pH6.3, 110 ug/ml; pH 5.9, 100 ug/ml; and pH 4.5, 800 ug/ml) and standards (Rainbow Markers, Amersham and Dalton Mark-VII, Sigma). Electrophoresis was performed at 20 mA constant current until the dye front entered the separating gel, and at 60 mA constant current until the dye front reached 0.5 cm from the bottom. The gels were then removed and one was fixed with 45% methanol/10% acetic acid for one hour, and the other was placed in transfer buffer (25 mM Tris, 192 mM glycine, 20% methanol, pH 8.3) for 20–30 minutes.

Silver Staining

The fixed gel was equilibrated with 2 changes of 10% ethanol/5% acetic acid for 30 minutes each. The gel was then exposed to a 0.0032N $HNO_3$/K2Cr2O7 solution for 5 minutes. The gel was washed in deionized water 3 times for 10 minutes each. The gel was impregnated with silver using 0.1 g $AgNO_3$/50 ml $H_2O$ for 30 minutes. The silver solution was washed off the gel in deionized water for 5 minutes. The gel was then exposed to a developer solution (29.7 g anhydrous $Na2CO_3$ in 1 liter $H_2O$ with 0.5 ml formalin) in 5 minute intervals between changes until the desired density was reached. The development was stopped with 10% acetic acid, and the gel stored in $H_2O$.

The gel showed a protein band of approximately 19 kD that was prominent in the bacterial lysate from transfected cells and in the elution fraction from pH 4.5 on nickel/NTA (FIG. 1). This protein was not represented in any of the other samples. This is consistent with the size of INGAP [protein] and with interaction of the inserted histidine tagging region with the nickel/NTA column matrix.

Western Blotting

Immobilon-P PVDF membrane was wetted with 100% methanol, and equilibrated with transfer buffer for 10 minutes. The gel was removed from transfer buffer and placed on the PVDF membrane. All bubbles between the membrane and the gel were removed. The combination was placed between Whatmann 3 mm filter paper wetted with transfer buffer and the whole "sandwich" was placed in the cassette of a Hoefer transfer tank. The cassette was placed in the transfer tank filled with transfer buffer with the gel toward the cathode. The transfer was performed at 12V constant voltage for 18 hours.

After transfer, the membrane was placed in a blocking buffer of 0.5M Tris, 2M NaCl and 1% polyethylene glycol with 5% bovine serum albumin and 10% goat serum at room temperature for 1 hour. The membrane was then placed into 20 ml of blocking buffer containing INGAP antibody 945-2 at a dilution of 1:5000 and incubated at room temperature for 1 hour. The membrane was then washed 3 times for 15 minutes each with 50 ml of washing buffer (0.4% Tween-20 in phosphate-buffered saline (PBS) at pH 7.4). The membrane was then incubated for 1 hour at room temperature in washing buffer containing anti-rabbit IgG (whole molecule, Sigma Cat #A-0545) peroxidase conjugate at a 1:160,000 dilution. The membrane was washed 3 times for 5 minutes in 50 ml of 0.2% Tween-20 in PBS, followed by 3 washes of 5 minutes each with 0.1% Tween-20 in PBS. The blot was revealed using the enzyme chemiluminescence kit from Amersham Corp., Arlington, Ill. according to instructions. The ECL blot was exposed to Kodak X-Omat AR-5 X-ray film for 20 minutes.

Figure 2:
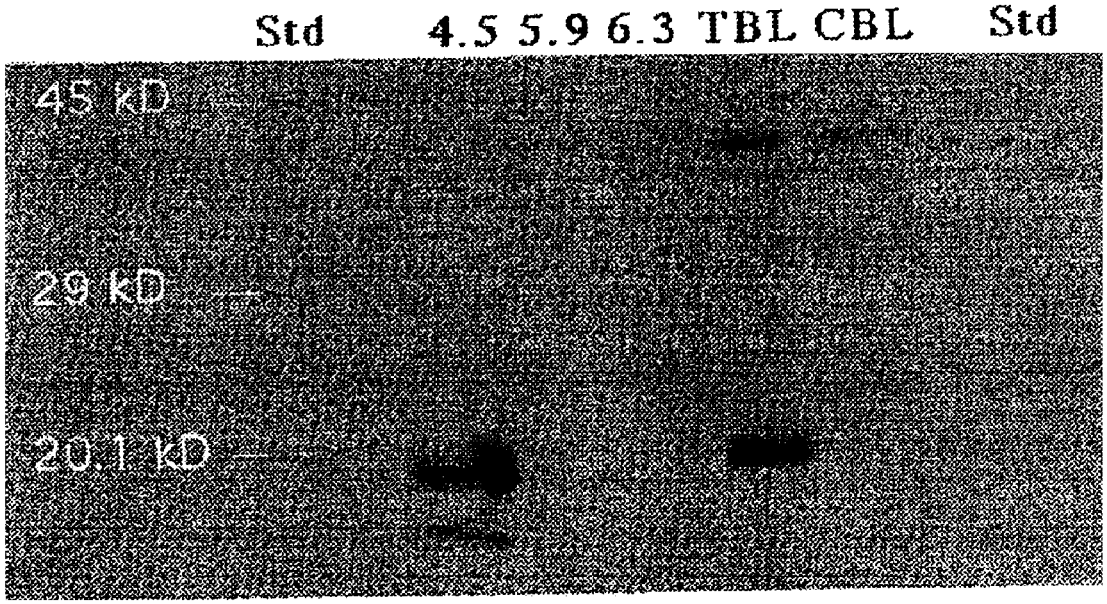
FIG. 2. ECL film of Western blot using INGAP antibody 945-2. Lanes are as identified in the description to FIG. 1.

ECL of the blot revealed strong protein recognition of the overexpressed 19 kD proteins in the whole lysate from transfected bacteria (IBL) and the pH 4.5 fraction that were visualized on the SDS-PAGE gels (FIG. 2). In addition, there was a protein band recognized in both bacterial lysates at 40 kD, implying that this protein is weakly recognized and is a bacterial protein rather than a product of the transfection. Finally, there was a light hand at 14 kD recognized by the antibody in both the transfected bacterial lysate and in the pH 4.5 fraction. This may either be another protein or a lytic fraction of [the] INGAP [protein]. Given the engineering done to produce [the] INGAP [protein] it is most likely a lytic fraction of INGAP.

In summary, we have been able to express INGAP [protein] in a prokaryotic system by excluding the 5' UTR and the signal peptide and insertion of the new construct into a new vector. The resultant protein is of the predicted molecular size of INGAP monomer and reacts with the antibody to INGAP in a Western analysis. The protein shares with INGAP peptide the ability to induce ductal cell proliferation.

EXAMPLE 6

This example describes the experimental design employed for INGAP expression in eukaryotic systems.

We generated an INGAP cDNA by PCR which excluded the 5' UTR region (nucleotides 1–16 in SEQ ID: 1) and nucleotides encoding the signal peptide (nucleotides 17–94 SEQ ID NO: 1). The reason for excluding the 5' UTR region was to create a protein that is similar to the native protein in which the 5' UTR is not part of the protein. We also created two new restriction enzyme recognition sites enabling the insertion of the new construct into a new pEBVHis-B eukaryotic expression vector. This new ligated construct was transformed into INVαF' competent cells (E. coli host strain from Invitrogen). The positive clones were identified, verified by restriction enzyme digestion and the DNA isolated and transfected into COS-7 cells. The His-tagged protein was isolated by $Ni^{+2}$ agarose affinity purification. The isolated protein showed biological activity when used to stimulate proliferation of ARIP (ductal) cells as measured by $^3$H-TdR incorporation.

We used a PCR approach to generate a new INGAP cDNA which excludes the 5' UTR region (nucleotides 1–16 in SEQ ID NO: 1) and nucleotides encoding the signal peptide.

The sequence (SEQ ID NO: 1) that has been excluded is as follows: (the bolded area represents the sequence of the signal peptide)

```
CTGCAAGACAGGTACCATG ATG CTT CCC ATG ACC CTC TGT
                MET MET Leu Pro MET The Leu Cys
AGG ATG TCT TGG ATG CTG CTT TCC TGC CTG ATG TTC
Arg MET Ser Trp MET Leu Leu Ser Cys Leu MET Phe
CTT TCT TGG GTG GAA GGT
Leu Ser Trp Val Glu Gly
```

To engineer the new INGAP construct we designed oligonucleotides corresponding to the 5' and 3' ends of the INGAP sequence to be amplified.

EXAMPLE 7

This example describes the use of polymerase chain reaction to synthesize INGMAT (construct which lacks the signal peptide sequence, i.e., which encodes the mature protein).

Oligonucleotide design

Oligonucleotides for PCR were designed to incorporate restriction enzyme recognition sites at their respective 5' ends. The oligonucleotide designed for the 5' end of the gene incorporates a Bam HI site followed by 20 nucleotides corresponding to the N-terminus of the mature protein. The oligonucleotide designed for the 3' end incorporates an Xho I site followed by 20 untranslated nucleotides. The PCR product generated from these primers contains the mature INGAP sequence and the native protein termination codon.

The following is the sequence of the oligonucleotides used:

5' of INGAP (SEQ ID NO: 2)

5'-CCGCGGATCCCGAAGAATCTCAAAAGAAACT-3'

3' of INGAP (SEQ ID NO: 3)

5'-GACCGGCTCGAGTGCTCTTCCTGAGTGAATCC-3'

PCR of INGMAT

Reaction conditions

| | |
|---|---|
| Template: (50 ng INGAP original cDNA removed from pCDNA3) | 5 μl |
| $MgCl_2$: | 4 μl |
| 10 × PCR buffer | 5 μl |
| dATP | 1 μl |
| dCTP | 1 μl |
| dGTP | 1 μl |
| dTTP | 1 μl |
| 5' primer | 1 μl |
| 3' primer | 1 μl |
| $H_2O$ | 29 μl |
| Taq polymerase | 1 μl |
| total volume = | 50 μl |

cycle parameters

A) 2 min at 95° C.

B) 30 cycles of (1 min 95° C., 1 min 55° C., 1 min 72° C.)

C) 7 min at 72° C.

D) 4° C. until removed from thermal cycler.

The PCR products were then electrophoresed on a 5% PAGE in TBE. Ethidium bromide stained PCR products corresponding to the expected size for the construct were cut from the gel. The gel fragments were electro-eluted into 0.5 ml of TBE, precipitated with 50 μl 3M sodium acetate and 1 ml of isopropanol at −80° C. for 20 min, centrifuged, washed once with 1 ml of isopropanol, washed once with 1 ml of 70% ethanol, and then dried under vacuum. The dried pellet was resuspended in 50 μl $H_2O$ and quantified. At the end of this step the sequence of the PCR product that contains both restriction sites minus the signal sequence and 5' UTR was as follows (SEQ ID NO: 4):

```
5'-CC GCG GAT CCC GAA GAA TCT CAA AAG AAA CTGCCT
TCT TCA CGT ATA ACC TGT CCT CAA GGC TCT GTA GAA TAT
GGG TCC TAT TGC TAT TCA CTG ATT TTG ATA CCA CAG ACC
TGG TCT AAT GCA GAA CTA TCC TGC CAG ATG CAT TTC TCA
GGA CAC CTG GCA TTT CTT CTC AGT ACT GGT GAA ATT ACC
TTC GTG TCC TCC CTT GTG AAG AAC AGT TTG ACG GCC TAC
CAG TAC ATC TGG ATT GGA CTC CAT GAT CCC TCA CAT GGT
ACA CTA CCC AAC GGA AGT GGA TGG AGG TGG AGC AGT
TCC AAT GTG CTG ACC TTC TAT AAC TGG GAG AGG AAC CCC
TCT ATT GCT GCT GAC CGT GGT TAT TGT GCA GTT TTG TCT
CAG AAA TCA GGT TTT CAG AAG TGG AGA GAT TTT AAT TGT
GAA AAT GAG CTT CCC TAT ATC TGC AAA TTC AAG GTC TAG
GGC AGT TCT AAT TTC AAC AGC TTG AAA ATA TTA TGA AGC
TCA CAT GGA CAA GGA AGC AAG TAT GAG GAT TCA CTC
AGG AAG AGC ACT CGA GCC GGT C-3'
*The bolded areas represent the primers.
```

EXAMPLE 8

This example describes the creation of a plasmid containing an expression construct for expression in eukaryotic systems.

Restriction enzyme digestion of the INGMAT PCR product and the pEBVHis-B vector We performed two parallel restriction enzyme digestion reactions using 2.5 μg of both the INGMAT PCR product and pEBVHis-B vector. INGMAT was digested with Bam HI and Xho I simultaneously in a 30 μl volume. pEBVHis-B was digested with Bam HI and Xho I simultaneously in a 30 μl volume. Both digestion reactions were carried out at 37° C. for a period of 4 hours. After the reactions were completed, 400 ng of each was electrophoresed on a 1.5% agarose gel and stained with ethidium bromide to assure complete digestion. The remainder (~2.1 μg) of both digestion reactions were passed over a sepharose G-50 column twice to remove the small DNA fragments followed by two equal volume phenol extractions. The extracted DNA was then precipitated with 2 volumes of ethanol and 1/10 volume 3M sodium acetate at −80° C. for 20 minutes, centrifuged, washed twice with 70% ethanol and dried under vacuum. The pellets were resuspended in 25 μl $H_2O$ and quantified.

The pEBVHis-B expression system was purchased from INVITROGEN Corp. San Diego, Calif.

Ligation of INGMAT into pEBVHis-B

INGMAT (Bam HI/Xho I) and pEBVHis-B(Bam HI/Xho I) have compatible ends suitable for ligation.

Ligation conditions using a 20:1 insert to vector molar ratio.

| | |
|---|---|
| pEBVHis-B(vector) 62 ng | 1 μl |
| INGMAT (insert) 80 ng | 4 μl |
| 10 × ligation buffer | 1 μl |
| 10 mM rATP | 1 μl |
| T4 Ligase 4u | 1 μl |
| $H_2O$ | 2 μl |
| final volume = | 10 μl |

The ligation reactions were conducted at 12° C. for 16 hours.

Transformation of the ligation reaction products into INVαF' competent E. coli

We removed 5 μl of the ligation reaction into 100 μl of competent INVαF' cells, (INVαF' cells were purchased from Invitrogen, San Diego, Calif.) with 0.5 μl of 500 mM β-mercaptoethanol and incubated on ice for 30 minutes, heat shocked for 45 seconds at 42° C., and recovered on ice for 2 minutes. Then we added 1 ml of prewarmed SOC media and incubated at 37° C. with shaking at 225 rpm for 1 hour followed by plating all the transformation reaction on LB broth agar plates containing 100 μg/ml ampicillin.

Selection of transformants

Six colonies were picked and grown up in LB broth with ampicillin. DNA was isolated from the small cultures using alkaline lysis extraction procedures, phenol extracted, precipitated, dried, and resuspended in 50 μl $H_2O$. Small aliquots of each of the isolated DNA were digested with Bam HI and Xho I to release insert. The digested DNA was run on 1.5% agarose gel and visualized by staining with ethidium bromide.

Several of the transformants that demonstrated the plasmid with inserts of the correct size were stored in 50% glycerol at −80° C. Large plasmid DNA stocks were isolated from 250 ml LB overnight cultures for use in COS-7 cell transfections.

COS7 transfection

The eukaryotic cell transfection was carried out according to method described by Chen and Okayama "High-Efficiency Transformation of Mammalian Cells by Plasmid DNA", Molecular and Cellular Biology, vol. 7, No. 8, August 1987, p 2745–2752).

COS-7 cells (SV40 transformed African green monkey kidney cells) were grown on twenty 150 mm diameter plates in culture medium (Dulbecco's modified Eagles medium, 10% fetal bovine serum, penicillin/streptomycin) to 80% confluency.

Each plate was washed twice with 10 mls of PBS, and 25 mls of fresh culture medium added. The DNA transfection mixture (2.5 ml) was added dropwise to each plate, swirled gently, and incubated overnight at 37° C.

DNA transfection mixture:

| | |
|---|---|
| pEBVHis-INGMAT 60 ng | 0.080 ml |
| $H_2O$ | 1.045 ml |
| 2.5 M $CaCl_2$ | 0.125 ml |
| 2XBES | 1.25 ml |
| Final volume = | 2.5 ml |

The transfection media was removed from the plates. The plates were then washed 3 times with culture medium, replenished with 25 ml of culture media, and incubated for 48 hrs. The plates were washed twice with PBS and trypsinized. The trypsinized cells were collected from groups of 5 plates, pelleted, and frozen with liquid nitrogen.

EXAMPLE 9

This example describes denaturing metal affinity protein chromatography isolation of his tagged-INGAP [protein] without signal peptide. (Procedure for 2 cell pellets from five 150 mm plates each of pEBVHis-INGMAT transfected COS-7 cells).

$Ni+^2$ NTA agarose preparation

Place 5 ml of the 50% slurry into a disposable 50 ml centrifuge tube. Centrifuge for 2 minutes at 800×g and discard the supernatant. Add 42 ml of sterile water, resuspend the resin. Centrifuge for 2 minutes at 800×G and discard the supernatant. Add 42 ml of sterile water, resuspend the resin. Centrifuge for 2 minutes at 800×G and discard the supernatant. Add 42 ml of binding/lysis buffer A (6M Guanidine HCl, 0.1M sodium phosphate, 0.01M Tris, pH 8.0) and resuspend the resin. Centrifuge for 2 minutes at 800×G and discard the supernatant. Add 42 ml of binding/lysis buffer A (6M Guanidine HCL, 0.1M sodium phosphate, 0.01M Tris, pH 8.0) and resuspend the resin. Centrifuge for 2 minutes at 800×G and discard the supernatant. Add 42 ml of binding/lysis buffer A (6M Guanidine HCL, 0.1M sodium phosphate, 0.01M Tris, pH 8.0) and resuspend the resin. Centrifuge for 2 minutes at 800×G and discard the supernatant. Bring the total volume up to 5 ml with buffer A. The slurry is now ready for the application of the transfected COS-7 cell extract.

Transfected COS-7 cells lysis and protein isolation

Resuspend the transfected cell pellets in 2.5 ml of lysis buffer A. (6M Guanidine HCL, 0.1M sodium phosphate, 0.01M Tris, pH 8.0). Combine two resuspensions into one for a final volume of 5 ml. The lysed cells were passed through an 18-gauge needle 4 times, transferred to a 15 ml centrifuge tube, and centrifuged for 15 minutes at 10,000×G. The supernatant was collected and 5 ml of prepared $Ni^{2+}$ NTA was added. The mixture was rotated for 45 minutes. The slurry was loaded onto a 1.6 cm diameter column and allowed to flow through by gravity.

Washes

Flow through 30 ml of buffer A. (No need to collect.) Flow through 30 ml of buffer B (8M Urea, 0.1M Sodium phosphate, 0.01M Tris, pH 8.0). (No need to collect.) but $A_{280}$ should be at or near zero before continuing, if not, then wash with more. Wash through 20 ml of buffer C, same as B but pH 6.3. Collect 3 ml fractions. Wash through 20 ml of buffer D, same as B but pH 5.9. Collect 3 ml fractions.

Wash through 20 ml of buffer E, same as B but pH 4.5. Collect 3 ml fractions. At this point the protein should be in one of the fractions taken. Read the absorbance at 280 of all the fractions to discern where the protein is. Fractions containing the protein were pooled, concentrated, and analyzed by Western blot to confirm identity of the protein.

This example describes an analytical technique confirming the identity of the product.

Biological activity of the expressed protein

The ability of the expressed protein to stimulate cell proliferation was tested on ARIP cells. These cells exhibited a 50% increase in $^3$H-TdR incorporation, at doses of the protein of 10–100 ng/ml.

In summary, we have been able to express INGAP [protein] in an eukaryotic system by excluding the 5'UTR and the signal peptide. The resultant protein is of the predicted molecular size of INGAP monomer and reacts with antibody to INGAP in a Western analysis. The protein shares with INGAP peptide the ability to induce ductal cell proliferation.

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
(A) LENGTH: 94 base pairs
(B) TYPE: nucleic acid
(C) STRANDEDNESS: single
(D) TOPOLOGY: linear (xi) SEQUENCE DESCRIPTION: SEQ ID NO: 1:

CTGCAAGACA GGTACCATGA TGCTTCCCAT GACCCTCTGT AGGATGTCTT GGATGCTGCT 60

TTCCTGCCTG ATGTTCCTTT CTTGGGTGGA AGGT 94

(2) INFORMATION FOR SEQ ID NO: 2:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO: 2:

CCGCGGATCC CGAAGAATCT CAAAAGAAAC T 31

(2) INFORMATION FOR SEQ ID NO: 3:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO: 3:

GACCGGCTCG AGTGCTCTTC CTGAGTGAAT CC 32

(2) INFORMATION FOR SEQ ID NO: 4:

(i) SEQUENCE CHARACTERISTICS:
(A) LENGTH: 558 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 4:

CCGCGGATCC CGAAGAATCT CAAAAGAAAC TGCCTTCTTC ACGTATAACC TGTCCTCAAG 60

GCTCTGTAGC CTATGGGTCC TATTGCTATT CACTGATTTT GATACCACAG ACCTGGTCTA 120

ATGCAGAACT ATCCTGCCAG ATGCATTTCT CAGGACACCT GGCATTTCTT CTCAGTACTG 180

GTGAAATTAC CTTCGTGTCC TCCCTTGTGA AGAACAGTTT GACGGCCTAC CAGTACATCT 240

GGATTGGACT CCATGATCCC TCACATGGTA CACTACCCAA CGGAAGTGGA TGGAAGTGGA 300

GCAGTTCCAA TGTGCTGACC TTCTATAACT GGGAGAGGAA CCCCTCTATT GCTGCTGACC 360

GTGGTTATTG TGCAGTTTTG TCTCAGAAAT CAGGTTTTCA GAAGTGGAGA GATTTTAATT 420

-continued

```
GTGAAAATGA GCTTCCCTAT ATCTGCAAAT TCAAGGTCTA GGGCAGTTCT AATTTCAACA    480

GCTTGAAAAT ATTATGAAGC TCACATGGAC AAGGAAGCAA GTATGAGGAT TCACTCAGGA    540

AGAGCACTCG AGCCGGTC                                                  558
```

(2) INFORMATION FOR SEQ ID NO: 5:

(i) SEQUENCE CHARACTERISTICS:
(A) LENGTH: 26 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 5:

```
Met Met Leu Pro Met Thr Leu Cys Arg Met Ser Trp Met Leu Leu Ser
 1               5                  10                  15

Cys Leu Met Phe Leu Ser Trp Val Glu Gly
            20                  25
```

(2) INFORMATION FOR SEQ ID NO: 6:

(i) SEQUENCE CHARACTERISTICS:
(A) LENGTH: 175 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 6:

```
Met Met Leu Pro Met Thr Leu Cys Arg Met Ser Trp Met Leu Leu Ser
 1               5                  10                  15

Cys Leu Met Phe Leu Ser Trp Val Glu Gly Glu Glu Ser Gln Lys Lys
            20                  25                  30

Leu Pro Ser Ser Arg Ile Thr Cys Pro Gln Gly Ser Val Ala Tyr Gly
        35                  40                  45

Ser Tyr Cys Tyr Ser Leu Ile Leu Ile Pro Gln Thr Trp Ser Asn Ala
    50                  55                  60

Glu Leu Ser Cys Gln Met His Phe Ser Gly His Leu Ala Phe Leu Leu
65                  70                  75                  80

Ser Thr Gly Glu Ile Thr Phe Val Ser Ser Leu Val Lys Asn Ser Leu
                85                  90                  95

Thr Ala Tyr Gln Tyr Ile Trp Ile Gly Leu His Asp Pro Ser His Gly
            100                 105                 110

Thr Leu Pro Asn Gly Ser Gly Trp Lys Trp Ser Ser Ser Asn Val Leu
        115                 120                 125

Thr Phe Tyr Asn Trp Glu Arg Asn Pro Ser Ile Ala Ala Asp Arg Gly
    130                 135                 140

Tyr Cys Ala Val Leu Ser Gln Lys Ser Gly Phe Gln Lys Trp Arg Asp
145                 150                 155                 160

Phe Asn Cys Glu Asn Glu Leu Pro Tyr Ile Cys Lys Phe Lys Val
                165                 170                 175
```

We claim:

1. A recombinant construct for expression of [Islet Neogenesis Associated Protein or INGAP activity] *a protein which stimulates islet cell neogenesis* comprising:

a first nucleotide sequence encoding amino acid[s] *residues* 27 to 175 as shown in SEQ ID NO: 6 operably linked to a transcriptional initiation site and a translational initiation site, wherein a second nucleotide sequence encoding a signal peptide is not present immediately 5' of said first nucleotide sequence.

2. The construct of claim 1 wherein nucleotides 1–16 of SEQ ID NO: 1 are not present 5' of said first nucleotide sequence.

3. The construct of claim 1 further comprising a third nucleotide sequence encoding a histidine tag.

4. The construct of claim 3 wherein the third nucleotide sequence is immediately 5' or 3' to said first nucleotide sequence.

5. The construct of claim 1 wherein the transcriptional initiation site is inducible.

6. The construct of claim 1 wherein the transcriptional initiation site is the lac promoter[/] *and* operator.

7. The construct of claim 1 [further comprising a promoter sequence] *wherein the transcriptional initiation site is* capable of initiating constitutive transcription.

8. The construct of claim 7 wherein the [promoter sequence] *transcriptional initiation site* is Rous sarcoma virus long terminal repeat (RSVLTR).

9. The construct of claim 1 further comprising a nucleotide sequence encoding a nuclear antigen.

10. The construct of claim 9 wherein the nuclear antigen is *Epstein-Barr nuclear antigen-1* (EBNA-1).

11. The construct of claim 1 further comprising an origin of replication.

12. The construct of claim 11 wherein the origin of replication is Epstein Bar Virus (EBV) origin of replication.

13. A method of producing biologically active Islet Neogenesis Associated Protein or INGAP [protein] from a recombinant host cell comprising the steps of:

culturing a host cell comprising a recombinant construct comprising a first nucleotide sequence encoding amino acid[s] *residues* 27 to 175 as shown in SEQ ID NO: 6 operably linked to a transcriptional initiation site and a translational initiation site, wherein a second nucleotide sequence encoding a signal peptide is not present immediately 5' of said first nucleotide sequence, and recovering protein from said cultured host cell.

14. The method of claim 13 wherein the construct further comprises a third nucleotide sequence encoding a histidine tag, and INGAP [protein] is purified using a nickel affinity matrix.

15. [A] *An isolated* host cell comprising a recombinant construct comprising a first nucleotide sequence encoding amino acids 27 to 175 as shown in SEQ ID NO: 6 operably linked to a transcriptional [iron] *initiation* site and a translational initiation site, wherein a second nucleotide sequence encoding a signal peptide is not present immediately [5+] *5'* of said first nucleotide sequence.

16. The construct of claim 1 wherein the first nucleotide sequence encoding amino acid[s] *residues* 27 to 175 comprises nucleotides 12–456 of SEQ ID NO: 4.

17. The method of claim 13 wherein the first nucleotide sequence encoding amino acid[s] *residues* 27–175 comprises nucleotides 12–456 of SEQ ID NO: 4.

18. The host cell of claim 15 wherein the first nucleotide sequence encoding amino acid[s] *residues* 27–175 comprises nucleotides 12–456 of SEQ ID NO: 4.

*19. The construct of claim 1 wherein the transcriptional initiation site is selected from the group consisting of: λcI promoter, tac promoter, trp promoter, and tet promoter.*

*20. The construct of claim 1 which comprises a nucleotide sequence as shown in SEQ ID NO: 4.*

*21. A pair of oligonucleotide primers for amplifying a coding sequence consisting of nucleotides 12 to 456 of SEQ ID NO: 4, wherein each of said oligonucleotide primers hybridizes to an opposite strand of a double-stranded INGAP template under conditions sufficient for amplifying, wherein a first of said oligonucleotide primers hybridizes to the 5' end of the coding sequence for mature human INGAP and the second of said oligonucleotide primers hybridizes to the 3' end of the nucleotide sequence encoding mature human INGAP under conditions sufficient for amplifying nucleotides 12 to 456 of SEQ ID NO: 4.*

*22. The pair of oligonucleotide primers of claim 21 wherein one primer has the nucleotide sequence shown in SEQ ID NO: 2 and one primer has the nucleotide sequence shown in SEQ ID NO: 3.*

*23. A method of making an expression construct for producing INGAP in a recombinant host cell, comprising the step of:*

*linking a transcription initiation site, a translation initiation site, and a coding sequence for mature human INGAP consisting of nucleotides 12 to 456 of SEQ ID NO: 4, to make an expression construct which is devoid of the signal sequence of the coding sequence of INGAP.*

*24. The method of claim 23 further comprising linking to said coding sequence for mature human INGAP a coding sequence for a histidine tag.*

*25. The method of claim 23 wherein the transcription initiation site is inducible.*

*26. The method of claim 25 wherein the transcription initiation site is selected from the group consisting of the lac promoter/operator, the tac promoter, the trp promoter, the λcI promoter, and the tet promoter.*

*27. The method of claim 23 wherein the coding sequence for mature human INGAP is obtained by amplification of a coding sequence consisting of nucleotides 12 to 456 of SEQ ID NO: 4.*

*28. The method of claim 27 wherein the amplification is performed using primers having sequences as shown in SEQ ID NO: 2 and SEQ ID NO: 3.*

*29. A recombinant construct for expression of a protein which stimulates islet cell neogenesis, comprising:*

*a first nucleotide sequence encoding mature human INGAP consisting of nucleotides 12 to 456 of SEQ ID NO: 4, said first nucleotide sequence being operably linked to a transcriptional initiation site and a translational initiation site, wherein a second nucleotide sequence encoding a signal peptide according to SEQ ID NO: 5 is not present immediately 5' of said first nucleotide sequence.*

*30. The construct of claim 29 wherein nucleotides 1–16 of SEQ ID NO: 1 are not present 5' of said first nucleotide sequence.*

*31. The construct of claim 29 further comprising a third nucleotide sequence encoding a histidine tag.*

*32. The construct of claim 29 wherein the third nucleotide sequence is immediately 5' or 3' to said first nucleotide sequence.*

*33. The construct of claim 29 wherein the transcriptional initiation site is inducible.*

*34. The construct of claim 33 wherein the transcriptional initiation site is the lac promoter/operator.*

*35. The construct of claim 29 wherein the transcriptional initiation site is capable of initiating constitutive transcription.*

*36. The construct of claim 35 wherein the promoter sequence is Rous sarcoma virus long terminal repeat (RSVLTR).*

*37. The construct of claim 29 further comprising a nucleotide sequence encoding a nuclear antigen.*

*38. The construct of claim 37 wherein the nuclear antigen is Epstein-Barr nuclear antigen-1 (EBNA-1).*

*39. The construct of claim 29 further comprising an origin of replication.*

*40. The construct of claim 39 wherein the origin of replication is Epstein Bar Virus (EBV) origin of replication.*

*41. The construct of claim 33 wherein the transcriptional initiation site is the λcI promoter/operator.*

*42. The construct of claim 33 wherein the transcriptional initiation site is the trp promoter.*

*43. The construct of claim 33 wherein the transcriptional initiation site is the tac promoter.*

*44. The construct of claim 33 wherein the transcriptional initiation site is the tet promoter.*

*45. A method of producing biologically active Islet Neogenesis Associated Protein (INGAP) from a recombinant host cell comprising the steps of:*

*culturing a host cell comprising a recombinant construct comprising a first nucleotide sequence encoding mature human INGAP consisting of nucleotides 12 to 456 of SEQ ID NO: 4 operably linked to a transcriptional initiation site and a translational initiation site, wherein a second nucleotide sequence encoding a signal peptide according to SEQ ID NO: 5 is not present immediately 5' of said first nucleotide sequence; and*

*recovering protein from said cultured host cell.*

*46. The method of claim 45 wherein the construct further comprises a third nucleotide sequence encoding a histidine tag, and INGAP is purified using a nickel affinity matrix.*

*47. A host cell comprising a recombinant construct comprising a first nucleotide sequence encoding mature human INGAP operably linked to a transcriptional initiation site and a translational initiation site, wherein a second nucleotide sequence encoding a signal peptide according to SEQ ID NO: 5 is not present immediately 5' of said first nucleotide sequence.*

*48. The method of claim 23 wherein the coding sequence for mature human INGAP encodes amino acid residues 27 to 175 as shown in SEQ ID NO: 6.*

*49. The pair of oligonucleotide primers of claim 21 wherein the first of said oligonucleotide primers comprises nucleotides 12 to 31 of SEQ ID NO: 2 and the second of said oligonucleotide primers comprises nucleotides 13 to 32 of SEQ ID NO: 3.*

* * * * *

UNITED STATES PATENT AND TRADEMARK OFFICE

CERTIFICATE OF CORRECTION

PATENT NO. : RE 39,351 E
APPLICATION NO. : 09/659379
DATED : October 17, 2006
INVENTOR(S) : Aaron I. Vinik et al.

It is certified that error appears in the above-identified patent and that said Letters Patent is hereby corrected as shown below:

On the Title page, Date of Reissued Patent item (45):
Please replace "Oct. 17, 2006" with --*Oct. 17, 2006--

On the Title page, Note item (*):
Please insert --This patent is subject to a terminal disclaimer.--

Column 19, Claim 16, Line 58:
Please replace "12-456" with --*12-458* [12-456]--

Column 19, Claim 17, Line 61:
Please replace "12-456" with --*12-458* [12-456]--

Column 19, Claim 18, Line 64:
Please replace "12-456" with --*12-458* [12-456]--

Column 20, Claim 21, Line 4:
Please replace "456" with --458--

Column 20, Claim 21, Line 13:
Please replace "456" with --458--

Column 20, Claim 23, Line 23:
Please replace "456"with --458--

Column 20, Claim 27, Line 38:
Please replace "456" with --458--

Column 20, Claim 29, Line 46:
Please replace "456" with --458--

UNITED STATES PATENT AND TRADEMARK OFFICE

CERTIFICATE OF CORRECTION

PATENT NO. : RE 39,351 E
APPLICATION NO. : 09/659379
DATED : October 17, 2006
INVENTOR(S) : Aaron I. Vinik et al.

It is certified that error appears in the above-identified patent and that said Letters Patent is hereby corrected as shown below:

Column 21, Claim 45, Line 26:
Please replace "456" with --458--

Signed and Sealed this

Twenty-sixth Day of February, 2008

JON W. DUDAS
*Director of the United States Patent and Trademark Office*